US00PP20746P3

(12) United States Plant Patent
Hall et al.

(10) Patent No.: US PP20,746 P3
(45) Date of Patent: Feb. 9, 2010

(54) RASPBERRY PLANT NAMED 'AWAROA'

(50) Latin Name: ***Rubus idaeus* L.**
Varietal Denomination: Awaroa

(75) Inventors: Harvey K. Hall, Motueka (NZ); Joseph Stephens, Auckland (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/214,404

(22) Filed: Jun. 18, 2008

(65) Prior Publication Data

US 2008/0320624 P1 Dec. 25, 2008

Related U.S. Application Data

(60) Provisional application No. 60/936,281, filed on Jun. 19, 2007.

(51) Int. Cl.
*A01H 5/00* (2006.01)

(52) U.S. Cl. ..... Plt./204

(58) Field of Classification Search ..... Plt./204
See application file for complete search history.

*Primary Examiner*—Susan B McCormick Ewoldt
(74) *Attorney, Agent, or Firm*—Greenlee Winner and Sullivan PC

(57) ABSTRACT

A new and distinct floricane fruiting red raspberry, *Rubus idaeus* L., variety is described. The variety results from selection among a population of seedlings derived from controlled pollination crossing of the unreleased raspberry selections with the breeder codes 86105N26 (not patented) and 87115ZN2 (not patented). This new variety is characterized by very early onset of fruit ripening. The new variety is distinguished from others by its high yields of firm and attractive conical shaped, uniform sized, large, red berries that ripen very early in the season. The plant exhibits a spine-free upright growth habit, of strong vigor. The new variety appears suitable for the fresh fruit market and the plant is also potentially well-adapted to machine harvesting. The variety has been named 'Awaroa'.

4 Drawing Sheets

Genus and species of plant claimed: *Rubus idaeus* L.

Variety denomination: Awaroa.

BACKGROUND TO THE INVENTION

The new variety of red raspberry, *Rubus idaeus* L., was created in the course of a planned breeding program carried out at Nelson, Motueka, New Zealand. The parents used to make the cross in 1991, were the unpatented selection 86105N26 (seed parent) and unpatented selection 87115ZN2 (pollen parent).

Seed from this cross was grown and the original plant of the new variety was selected during the 1994–95 summer (Southern Hemisphere) and was found to exhibit:

(a) a spine-free upright growth habit of strong vigor, (b) the ability to form attractive red fruit of good flavor that ripen very early on floricanes and (c) the ability to form attractive red fruit of good flavor on primocanes late in the season and (d) resistance to Raspberry Bushy Dwarf Virus (RBDV).

The new variety was first asexually propagated in 1999, at Motueka, Nelson, New Zealand, being reproduced by vegetative cuttings arising from root cuttings. Cuttings developed this way in spring, root within a 3–4 week propagation period, and thus plants suitable for field planting are then ready in autumn of the same year. The resulting plants propagated true to type, demonstrating that the characteristics of the new variety are stable and are transmitted without change through succeeding generations. Since 2000, 'Awaroa' has been asexually propagated in vitro via tissue culture methods. The variety has propagated true to type via these means.

SUMMARY OF THE INVENTION

The new variety was selected from a population of seedlings derived from crossing the unreleased raspberry selections with the breeder codes 86105N26 (not patented) and 87115ZN2 (not patented). The new variety was assigned the breeder code, 91355VF.9 (subsequently coded HR137 at the advanced selection stage). The new variety has since been named 'Awaroa'.

The new variety was tested and evaluated during the years 1996 to 2005 in the Nelson Region, New Zealand (41.10°S, 172.97°E).

When compared to the parent 86105N26, fruit of the new variety was found to be softer and plant canes were more upright and vigorous. 'Awaroa' was also found to produce more fruit on primocanes than 86105N26.

When compared to the parent 87115ZN2, the new variety exhibits fruit that are larger and the plant produced more fruit on primocanes.

Data collected during the evaluation period comparing fruiting performance of the new variety with standard New Zealand varieties and other varieties is presented in Table 1.

TABLE 1

Comparison of fruiting and shelf life performance.

| | 2003/04 season | | | 2005/06 season | | |
|---|---|---|---|---|---|---|
| Variety | Yield[1] (T/ha) | Berry weight (g) | Shelf life[2] | Yield[1] (T/ha) | Berry weight (g) | Shelf life[2] |
| 'Tadmor' | 25.9 | 4.5 | 36 | 13.7 | 4.7 | 50 |
| 'Korpiko' | 14.8 | 4 | 45 | 17.2 | 5.3 | 27 |
| 'Tulameen' | 17.1 | 4.1 | 63 | 12.9 | 4.2 | 76 |
| 'Motueka' | 21.3 | 2.7 | | 15.3 | 3.8 | |
| 'Moutere' | 17.4 | 3 | 63 | 14.2 | 4.5 | 48 |
| 'Korere' | 19.5 | 2.8 | 30 | 13.20 | 3.80 | 48 |
| 'Awaroa'[3] | 15.6 | 3.1 | | 14.4 | 4.1 | 62 |

[1]Hand-picked
[2]Mean (10 berries × 3 reps × 3 harvests) cumulative percentage of berries with rot caused by *Botrytis* after 72 hours on the shelf at ambient temperatures (15-20° C.).
[3]'Awaroa' is a dual cropper i.e. the fruit is borne on both the current and previous year's growth; the data shown in Table 1 indicates the floricane fruit yield only.

Berries of the new variety are suitable for consumption as early season fresh fruit. While unconfirmed it is likely that 'Awaroa' will also be suited to machine harvesting operations as fruit are easy to remove from the receptacle.

BRIEF DESCRIPTION OF THE DRAWINGS

The accompanying photographs show typical specimens of the plant, foliage and fruit of the new variety as depicted in colors as nearly true as is reasonably possible to make the same in a color illustration of this character.

DETAILED DESCRIPTION

Figure 1:
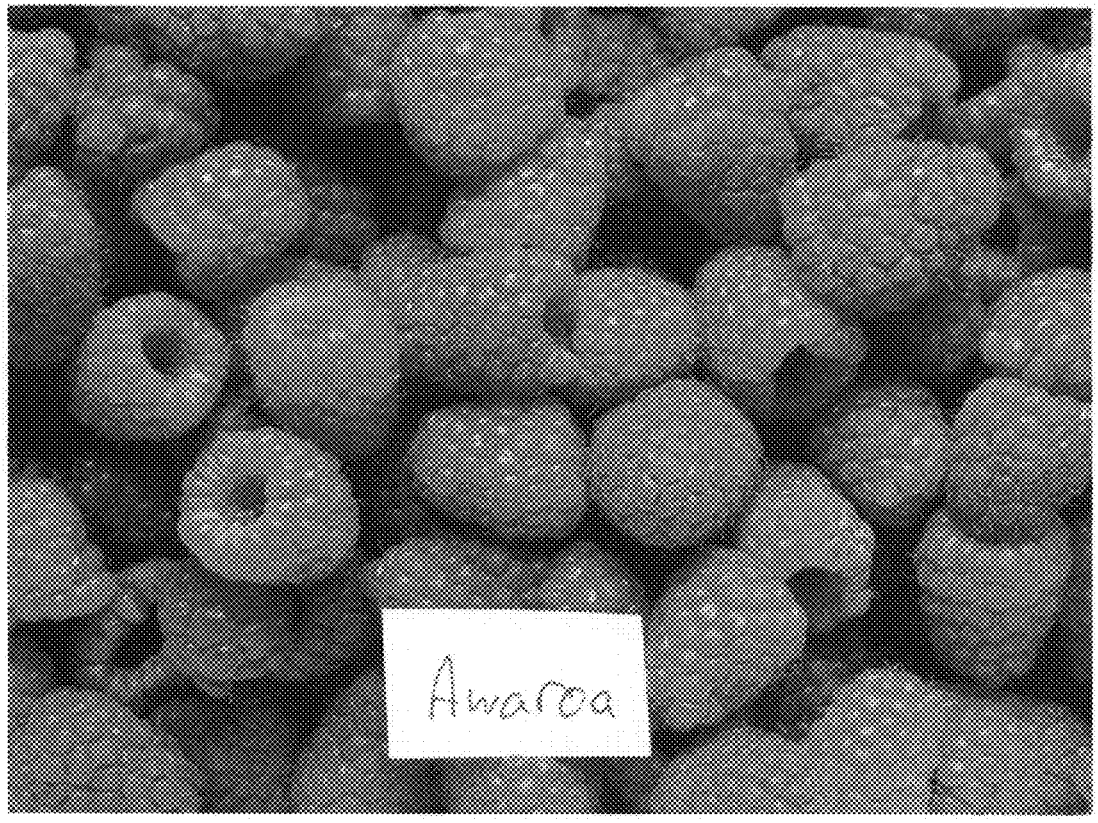
FIG. 1 shows close-up views of typical fruit of the variety 'Awaroa'.

Horticultural terminology is used in accordance with UPOV guidelines for raspberry. All dimensions in millimeters, weights in grams (unless otherwise stated). Where a color reference is given these refer to The R.H.S. Colour Chart, The Royal Horticultural Society, London. 4$^{th}$ Edition, 2001. The specimens described were grown at Nelson, New Zealand.

Environmental data for the New Zealand growing area demonstrates conditions in spring and early summer (equating to the harvest period for the cultivar) as follows:

Spring (September/October); mean daily temperature in the range 10–12° C. (mean daily minimum 5.8° C., mean daily maximum 16.5° C.).

Early summer (December/January); mean daily temperature 16.8° C. (mean daily minimum 11.1° C., mean daily maximum 22.4° C.).

A cool temperate area, frost conditions are typically experienced in winter, with the lowest winter air temperature unlikely to be colder than −6° C. Average annual rainfall is approximately 1125 mm.

Figure 3:
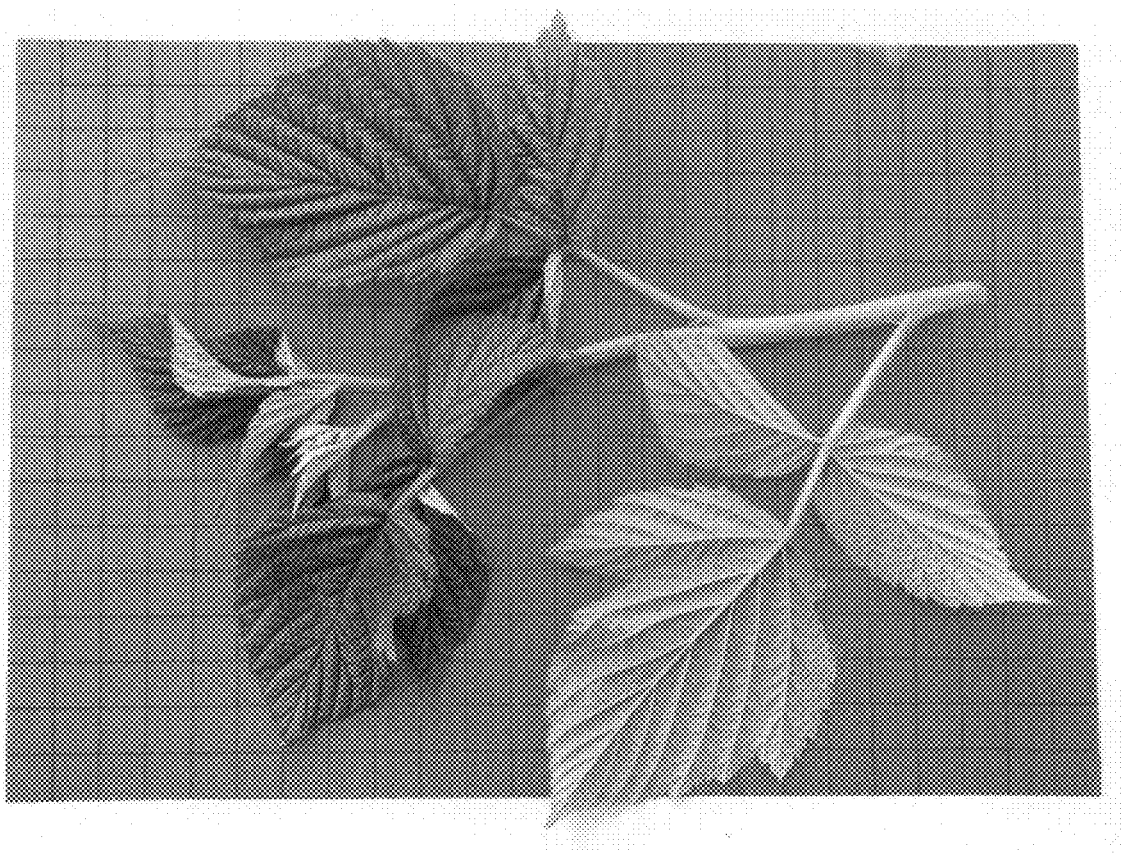
FIG. 3 shows the leaf and shoot tip of a fruiting lateral of the variety 'Awaroa'; view is of the upper and lower surfaces.
Figure 4:
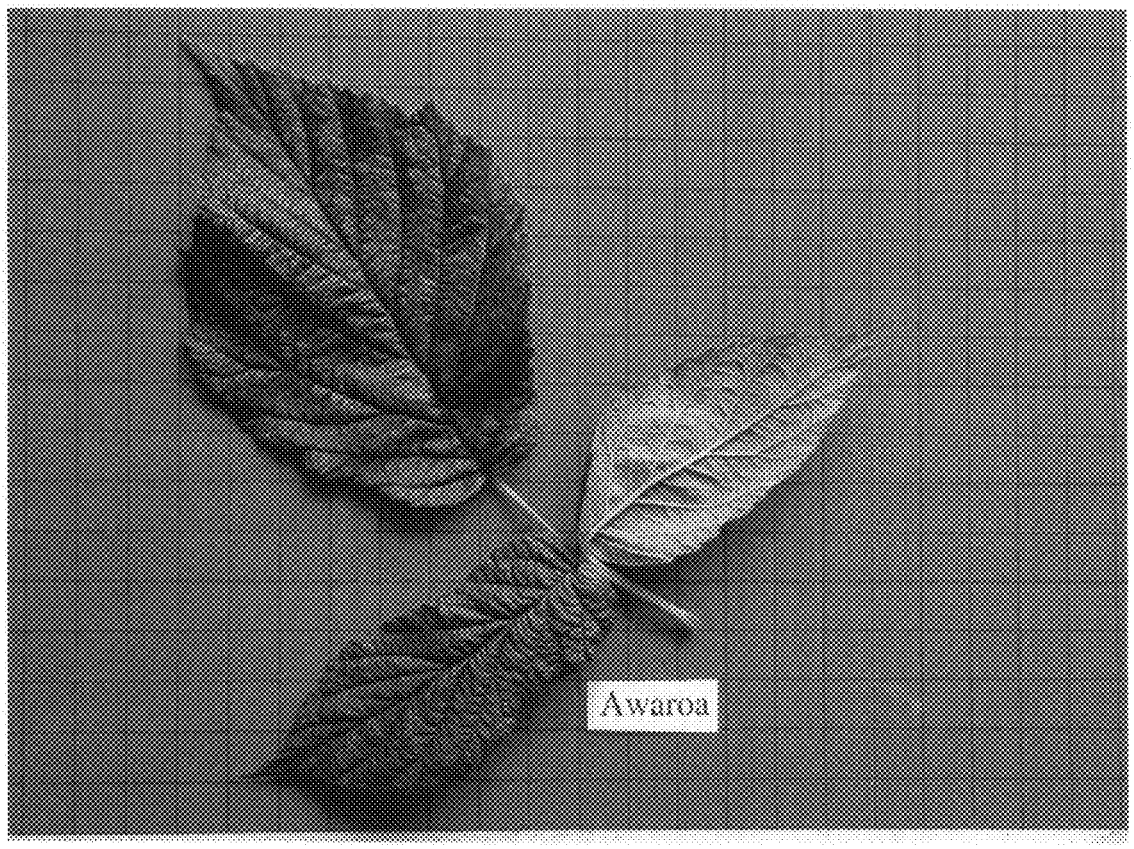
FIG. 4 shows a floricane leaf of the variety; view is of both the upper and lower leaf surfaces.

Plant and foliage: Plants exhibit medium vigor and are upright in growth habit. Mature plant height averages approximately 2000 to 2200 in height, although this may vary with the growing conditions. Although good vigor is exhibited, internode length is quite short, typically in the range 40–50 mm. Plants have many young shoots and canes have no spines. Plants of 'Awaroa' have been observed to be less spiny compared with some other commercial varieties, for instance, 'Skeena' (not patented) which has few spines. Fruiting laterals are medium length. Canes are not pubescent indicating the absence of gene H. Canes typically show light brown-tan coloration (near Greyed-orange 175A and 175C) in winter. During the growing season some purple coloration (near Red-purple 59A) is evident on the sun-exposed side of the cane. Young shoots are erect, numerous in number, and are near Yellow-green 144A in color. The leaves are compound, moderately crinkled, flat and glossy, with strong silver coloration on the leaf underside (FIGS. 3 and 4). The number of primocane leaflets per internode is both three and five. The base of the terminal leaflet is concave in shape and typically average 60 mm in diameter and 90 mm in length. The coloration of the upper surface of the leaf is green (near Green 137A), the under side being markedly lighter in coloration (near Greyed-green 194A). While the leaves do not have distinguished marginal or vein coloration, the venation has noticeable rises and falls, and the leaf margin is typically serrate. The leaf petiole typically averages approximately 40–50 mm in length and 2.3 mm in diameter. It is near Yellow-green 145B in color. The fruiting laterals are medium short in length, commonly measuring 300–400 mm, and are weakly ascending and horizontal when fruit has ripened. Fruit presentation at harvest time is excellent and well suited to hand-picking.

Infloresence: White flowers on short, slender pedicels. Flowers are numerous and borne on a paniculate inflorescence. Typically there are five petals, elongated ovate in shape with a rounded apex and flat base. They are typically smooth in texture, have a smooth margin and are near White 155C in color. The flowers are predominantly borne singly, although sometimes in clusters of two or more. Terminal branch flower clusters frequently consist of two flowers and basal flower clusters may number three to five. The flowers have no discernible fragrance. Five sepals are present. The reproductive organs are typical for flowers of *Rubus idaeus* L.; stigmas, many; stamens numerous.

Bloom period: Early season, late summer. In the Nelson Region, New Zealand, bud burst on floricanes commences very early, approximately mid August. The time of bloom is early season for a summer fruiting raspberry.

Harvest: 'Awaroa' is capable of producing a dual crop; fruit is produced on previous year's cane in summer although the variety has a very early fruiting season and also produces some primocane crop (fruit on current year's cane in autumn). Fruit commences ripening on previous year's cane in mid November at Nelson, New Zealand. The typical start date for picking the new cultivar is November 15. Fifty percent of the harvest is typically completed by December 5, and the main harvest period is complete by late December (approximately December 31). The early time of fruit ripening has been observed to occur in conjunction with early bud break and a relatively short time from flowering until the onset of fruit ripening. This is a key distinguishing feature of the variety. The fruit ripening period on previous year's cane for 'Awaroa' has been observed to be earlier than for other commercial varieties regarded as early season varieties in production in New Zealand, for instance, 'Glen Moy' (not patented). 'Awaroa' is suited to harvest by hand and although untested is likely to be suited to machine harvest as well due to relative easy release of fruit from the plug. 'Awaroa' is recommended for very early season production for the fresh market fruit. As well, plants of 'Awaroa' have the potential to produce a commercially significant quantity of fruit on primocanes in the late season in certain environments under management to promote this characteristic.

Figure 2:
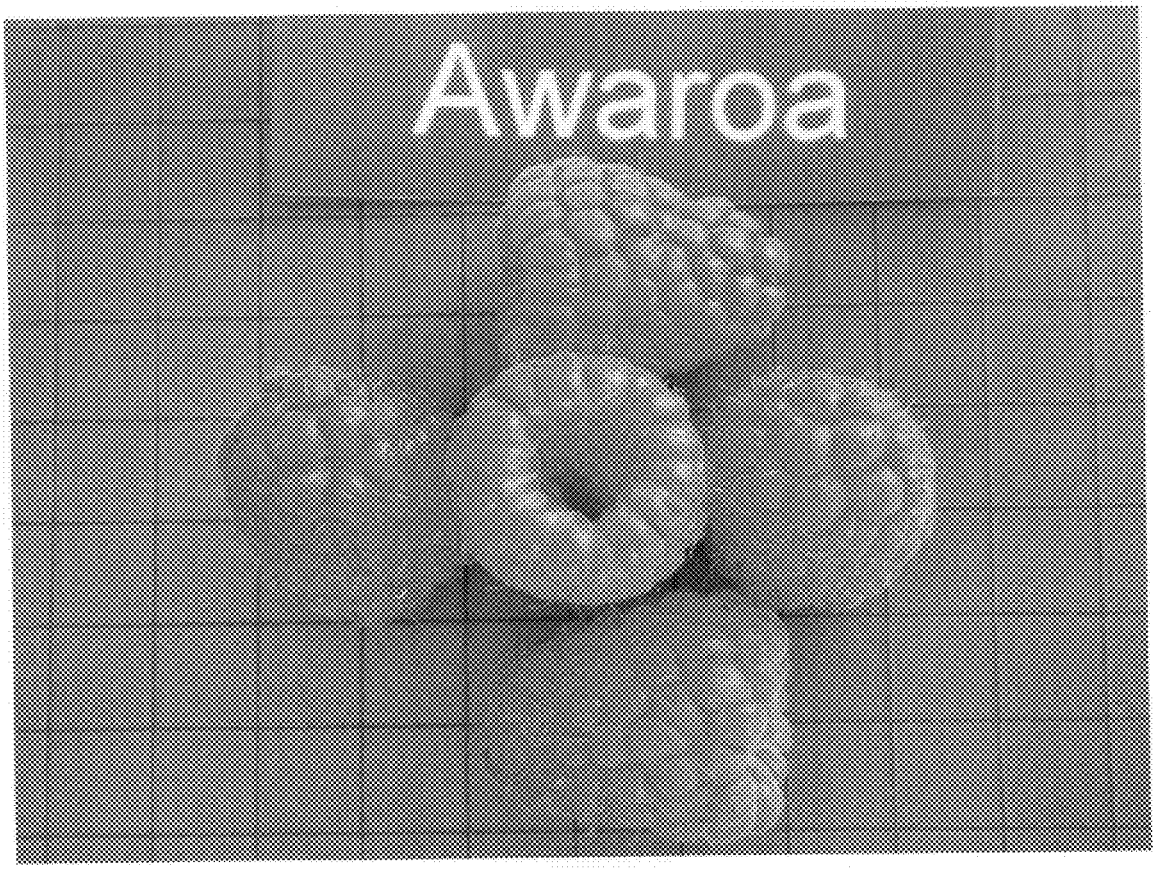
FIG. 2 shows enlarged, close-up, side and end views of a sample of individual fruit of the variety 'Awaroa'; photographed on a 1 cm×1 cm grid.

Fruit: The fruit is borne on both the current (primocane) and previous year's (floricane) growth. Berry size is medium. The average berry weight is approximately 4.0 g; individual fruit ranging between 3.0–4.0 g in weight (Table 1). Fruit shape is ovate; on the basis of fruit length to width ratio, fruit is longer than broad (FIG. 2). On average berries are 20–25 mm long and 20 mm wide at the widest point. Fruit color is light mid-red; external color near Red-53A, internal color near Red 46A. The berries have medium glossiness. Drupelets number typically 95–100 and are typically 4.1 mm in diameter. The berries are medium firm and of good raspberry flavor. The seeds average 3.0 mm long and 1.5 mm wide, and are near Greyed-orange N170C in color when dry. Seed numbers per fruit average 95–100 and weigh on average 0.19 g per fruit (or on average individually 1.9 mg). Fruit quality is largely due to the fruit having firm and fleshy texture with moderate flavor. 'Awaroa' fruit has been observed to have a moderate shelf life in the Nelson Region, New Zealand (Table 1). Yield is moderate on previous year's cane (expected to average up to 10–17 t/ha), and primocane yield is expected to be in the range 3–5 t/ha.

Pest and disease resistance: The plant appears to be resistant to Raspberry Bushy Dwarf Virus (RBDV). Since the selection of this clone in 1994-95 numerous tests for RBDV have been carried out on 'Awaroa' in New Zealand using ELISA, but on no occasion has the virus been detected in spite of high infection pressure. From this we suggest that 'Awaroa' is likely to be resistant to the common strain of RBDV found in New Zealand. The plant does not seem to be susceptible to yellow rust *Phragmidium rubi-idaei.* Resistance to aphids is unknown.

Geographical adaptation: Observations indicate that the variety is suitable for warmer regions where the risk of late spring frosts is reduced, and indications are the variety is adapted to regions where winter chill is not readily accumulated. For example, 'Awaroa' performs well in the cool temperate climate of the Nelson region under standard management practices for commercial raspberry production. The plant hardiness range compared with the USDA Plant Hardiness zones (published as the 2003 US National Arboretum "Web Version" of the USDA Plant Hardiness Zone Map USDA Miscellaneous Publication No. 1475, Issued January 1990) has not been determined. Under New Zealand conditions, the plants are grown in areas that experience some winter cold and frost, estimated to be equivalent to the minimum temperature range of zones 8–10.

We claim:

1. A new and distinct red raspberry plant as herein illustrated and described.

* * * * *